United States Patent
Kim et al.

(10) Patent No.: US 8,481,305 B2
(45) Date of Patent: *Jul. 9, 2013

(54) ROTATION DRIVING DEVICE FOR CELL CULTURING

(75) Inventors: Kyung Suk Kim, Seoul (KR); Jai Jun Choung, Seoul (KR)

(73) Assignee: Corestem Co., Ltd., Chungcheongbuk-do (KR)

( * ) Notice: Subject to any disclaimer, the term of this patent is extended or adjusted under 35 U.S.C. 154(b) by 421 days.

This patent is subject to a terminal disclaimer.

(21) Appl. No.: 12/744,718

(22) PCT Filed: Nov. 28, 2008

(86) PCT No.: PCT/KR2008/007036
§ 371 (c)(1),
(2), (4) Date: May 26, 2010

(87) PCT Pub. No.: WO2009/069961
PCT Pub. Date: Jun. 4, 2009

(65) Prior Publication Data
US 2010/0304474 A1      Dec. 2, 2010

(30) Foreign Application Priority Data

Nov. 30, 2007  (KR) .................. 10-2007-0123913

(51) Int. Cl.
*C12M 1/22* (2006.01)
*C12M 3/00* (2006.01)
(52) U.S. Cl.
USPC .............. 435/305.1; 435/286.3; 435/286.5; 435/288.3; 435/303.1; 435/299.2; 435/304.3; 435/304.1; 435/309.1; 435/307.1

(58) Field of Classification Search
USPC .......... 435/286.3, 286.5, 288.3, 303.1, 299.2, 435/304.3, 304.1, 305.1, 309.1, 307.1
See application file for complete search history.

(56) References Cited

U.S. PATENT DOCUMENTS

| 5,591,627 A | 1/1997 | Miyamoto |
| 5,624,185 A * | 4/1997 | Whisson ................ 366/141 |
| 5,639,160 A * | 6/1997 | Kishimoto ............. 366/208 |
| 2004/0151064 A1 | 8/2004 | Yi |
| 2005/0186669 A1 | 8/2005 | Ho et al. |

OTHER PUBLICATIONS

International Search Report from International Application No. PCT/KR2008/007036, dated Apr. 2, 2009.

* cited by examiner

*Primary Examiner* — Nathan Bowers
(74) *Attorney, Agent, or Firm* — Clark & Elbing LLP

(57) ABSTRACT

The present invention relates to a rotation driving device for cell culturing, comprising: a power supplying unit operated by receiving an electric power from an outside; a rotational part rotated by the power supplying unit; and a driving part which is provided at an upper side of the rotational part and maintained in a stopped state during the rotation of the rotational part, and of which an inclination is changed according to a rotational direction of the rotational part. According to the present invention, there is provided a rotation driving device a rotation driving device which enables cells to be uniformly grown by equally distributing a culture solution with help of inclination control, of which a rotational speed is also controlled and which has a firm structure with a strong durability.

9 Claims, 8 Drawing Sheets

ROTATION DRIVING DEVICE FOR CELL CULTURING

CROSS-REFERENCE TO RELATED APPLICATIONS

This application is the U.S. national stage filing under 35 U.S.C. §371 of international application PCT/KR2008/007036, filed Nov. 28, 2008, which claims benefit of Korean Patent Application 10-2007-0123913, filed Nov. 30, 2007.

BACKGROUND OF THE INVENTION

1. Field of the Invention

The present invention relates to a rotation driving device which can move regularly for cell culturing, particularly to a rotation driving device which enables cells to be uniformly grown by equally distributing a culture solution with help of inclination control, of which a rotational speed is also controlled and which has a firm structure with a strong durability.

2. Background of Technique

Cell culture comprises aseptically cutting off tissue sections from multicellular organisms and providing nutritive components to them, followed by incubation for cell proliferation in a vessel. The tissues of plants can be immortally proliferated.

A cell culture method includes a coverglass method, a flask method, a rotating tube method and the like. Generally, endosperm, leukocyte or spleen extracts are used to promote the growth of cultured tissues while its essential materials are not clearly elucidated yet. Recently, an antibiotic or an eagle culture solution containing vitamins and amino acids are often used.

The tissue culture permits a single cell to culture to a cell population, a small organ or a plant tissue.

The culture of living cells in a test tube is performed for various purposes, for example, recovery of additional by-products generated by cellular metabolisms, preparation of virus vaccines, culture of cells to fabricate an artificial organ, production of medicines by manipulating genes of an animal cell, breeding of a plant by cell fusion.

A suitable space for culturing cells, a culture solution for supplying nutritions to them, and various gases are required for cell culture. Certainly, it is also the same in the plant cells.

Particularly, the culture solutions and various gases are injected into the culture space and used for culturing cells, following the periodical exchange with new ones to maintain the cell tissues in a fresh condition.

Therefore, a cell culture device is essentially provided with a construction to supply and discharge the culture solutions and the various gases continuously and smoothly.

Using the cell culture device as described above, the cells in the culture space are irregularly distributed on a plane surface by flowing of the culture solution injected into the culture space. Therefore, it is difficult to properly supply the culture solution and gases to the cells and to uniformly grow the cells in the culture space.

Generally, a cultivator operates the cell culture device to overcome the problems. However, it is difficult to operate the cell culture device for a long time period in the sense of cost and concentration and also to uniformly distribute the cells.

Even though a separate driving unit is used to operate the cell culture device, it can only move the cell culture device up and down or from side to side. Thus, it is also limited to uniformly distribute the cells in the culture space and the driving unit repeats is easily out of order due to simple motion.

DETAILED DESCRIPTION OF THE INVENTION

It is an object of the present invention to provide a rotation driving device in which cells is uniformly grown by equally distributing a culture solution through an inclination control, and a rotational speed is controlled and has a firm structure with a strong durability.

To achieve the above object, the present invention provides a rotation driving device for cell culturing, comprising: a power supplying unit operated by receiving an electric power from an outside; a rotational part rotated by the power supplying unit; and a driving part which is provided at an upper side of the rotational part and maintained in a stopped state during the rotation of the rotational part, and of which an inclination is changed according to a rotational direction of the rotational part.

Preferably, the power supplying unit comprises a motor operated by the external electric power.

Preferably, the rotational part comprises: a rotational shaft which is fixed with the power supplying unit at its one end and is rotated by the electric power supplied by the power supplying unit; a circular plate type first supporting part attached to a lower end of the rotational shaft to support it for its rotation; a circular plate type second supporting part which is disposed at an upper side of the first supporting part and connected with the first supporting part through a plurality of hinge members and which is formed with an opening at a center portion thereof; a ball bearing receiving part which is formed on a circumference of an upper surface of the second supporting part and with a spherical recessed portion to receive a part of a ball bearing; and a ball bearing which is received in the ball bearing receiving part to be rolled.

Preferably, the rotation driving device further comprises a first supporting part fixing portion which is provided at a lower side of the first supporting part to fix the first supporting part.

Preferably, the rotational shaft is formed into a rod shape with a circular section, and the other end of the rotational shaft, which is not fixed to the power supplying unit, has a spherical shape.

Preferably, the ball bearing receiving part is formed at least three places on the circumference of the upper surface of the second supporting part to be spaced apart from each other in regular intervals.

Preferably, the hinge member is provided between the first and second supporting parts so that a central axis thereof is positioned at a center portion of both contacting portions and thus an angle thereof is controlled in both directions.

Preferably, the driving part comprises: a circular plate type cell culture device receiving part which has an installation space to equip the cell culture device; and a power transmitting part of which an upper surface is fixed to a bottom surface of the cell culture device receiving part and a lower surface has a spherical recessed portion in which the spherical end of the rotational shaft of the upper rotational part is pivotably inserted.

Preferably, the lower surface of the cell culture device receiving part is contacted with a ball bearing passage formed along a circumference thereof to have an appropriate width so that the ball bearing of the rotational part can be rolled.

Preferably, a plurality of grooves is formed at a side surface of the cell culture device receiving part to be detachable to the cell culture device in an easy manner.

According to the present invention described above, there is provided a rotation driving device for cell culturing to provide a rotation driving device in which cells is uniformly grown by equally distributing a culture solution through an inclination control, and a rotational speed is controlled and has a firm structure with a strong durability.

DETAILED DESCRIPTION OF MAIN ELEMENTS

10: motor
20: first supporting part
25: first supporting part receiving portion
30: second supporting part
35: hinge member
38: rotational shaft
40: ball bearing receiving part
45: ball bearing
50: rotational part
60: cell culture device receiving part
70: power transmitting part
80: driving part
90: cell culture device
100: rotation driving device

EXAMPLES

The objects, characters or other advantages of this invention described above will become apparent to those skilled in the art by explaining the preferable Examples of the present invention in detail referring to the appended drawings. The rotation driving device for cell culturing according to the Examples of the present invention will be described in further detail together with the appended claims and drawings below.

Figure 1:
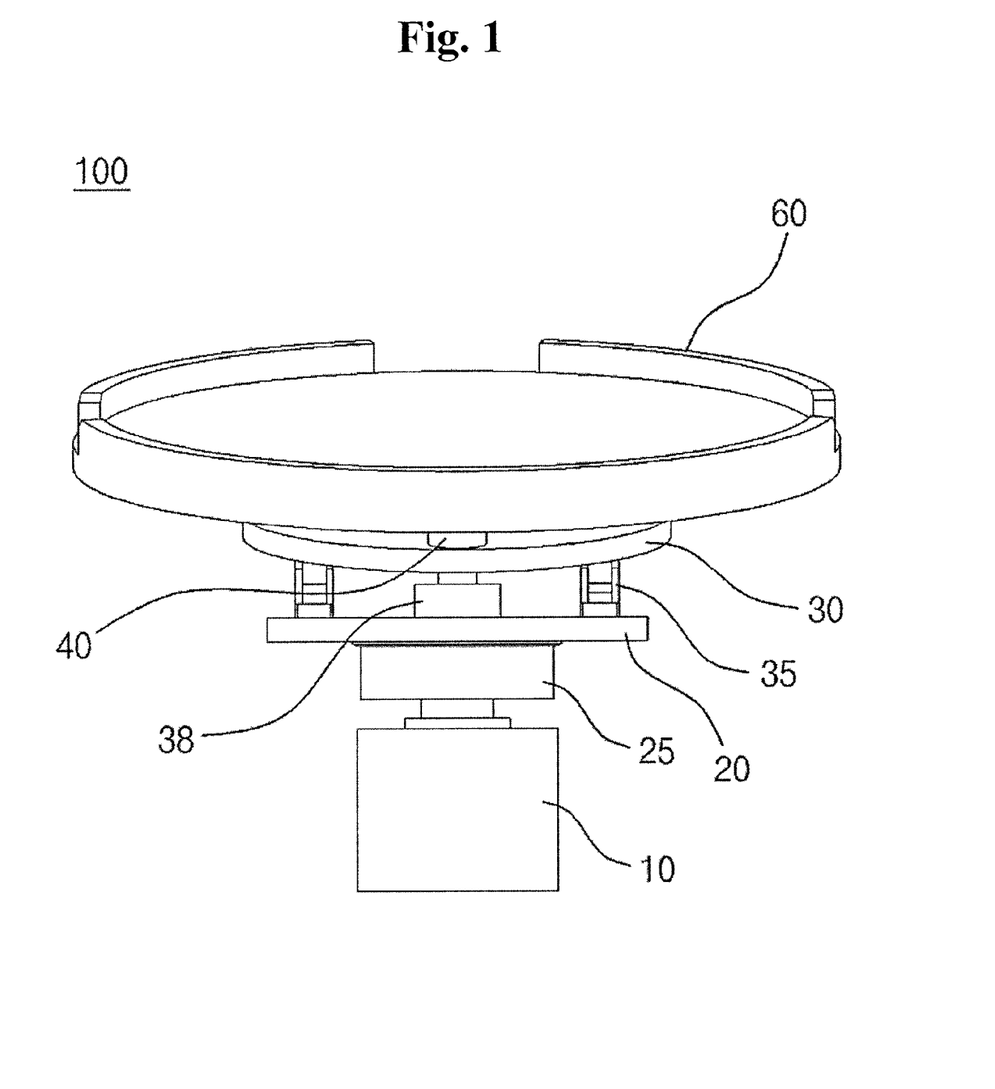
FIG. 1 is a perspective view of a rotation driving device for cell culturing.
Figure 2:
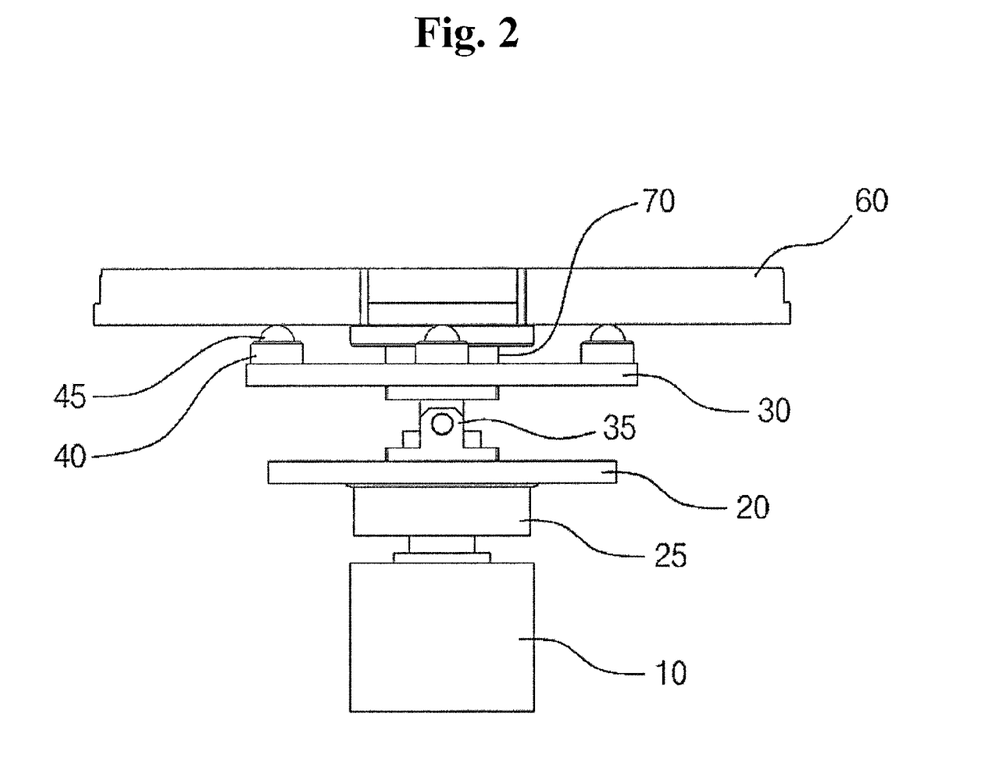
FIG. 2 is a side view of the rotation driving device for cell culturing.

FIG. 1 represents a perspective view of a rotation driving device (100) for cell culturing and FIG. 2 is a side view of the rotation driving device (100) for cell culturing.

Referring to FIGS. 1-2, the rotation driving device (100) for cell culturing according to the present invention includes a motor (10) to receive an electric power from an outside for its operation, a rotational part (50) to be rotated by the motor (10), and a driving part (80) which is disposed at an upper side of the rotational part (50) and only an inclination thereof is changed in a stopped state during the rotation of the rotational part (50).

It is also possible to use other power supplying units such as an electromotor or a generator instead of the motor (10).

The rotational part (50) is rotated by the motor (10), and the driving part (80) is operated to be corresponding to the rotational part (50) but maintained in the stopped state regardless of the rotation of the rotational part (50).

Figure 3:
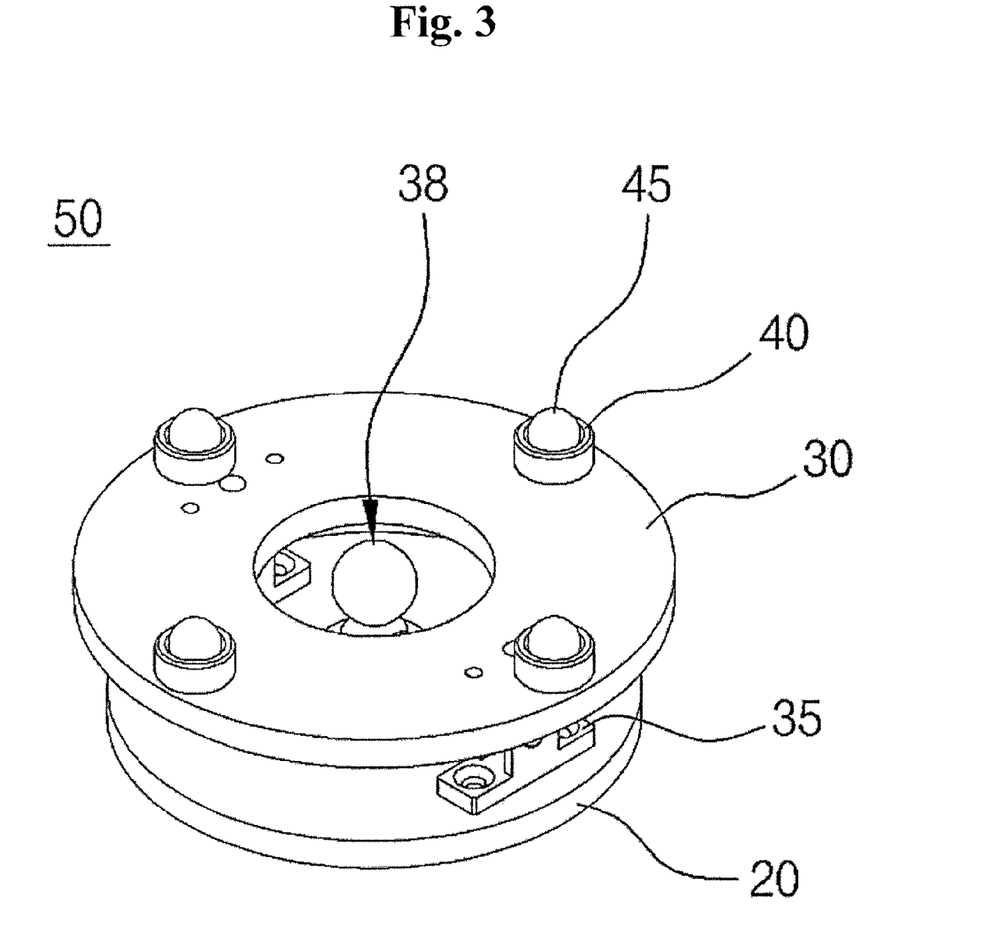
FIG. 3 is a perspective view of a rotating part of the rotation driving device for cell culturing as shown in FIG. 1.
Figure 4:
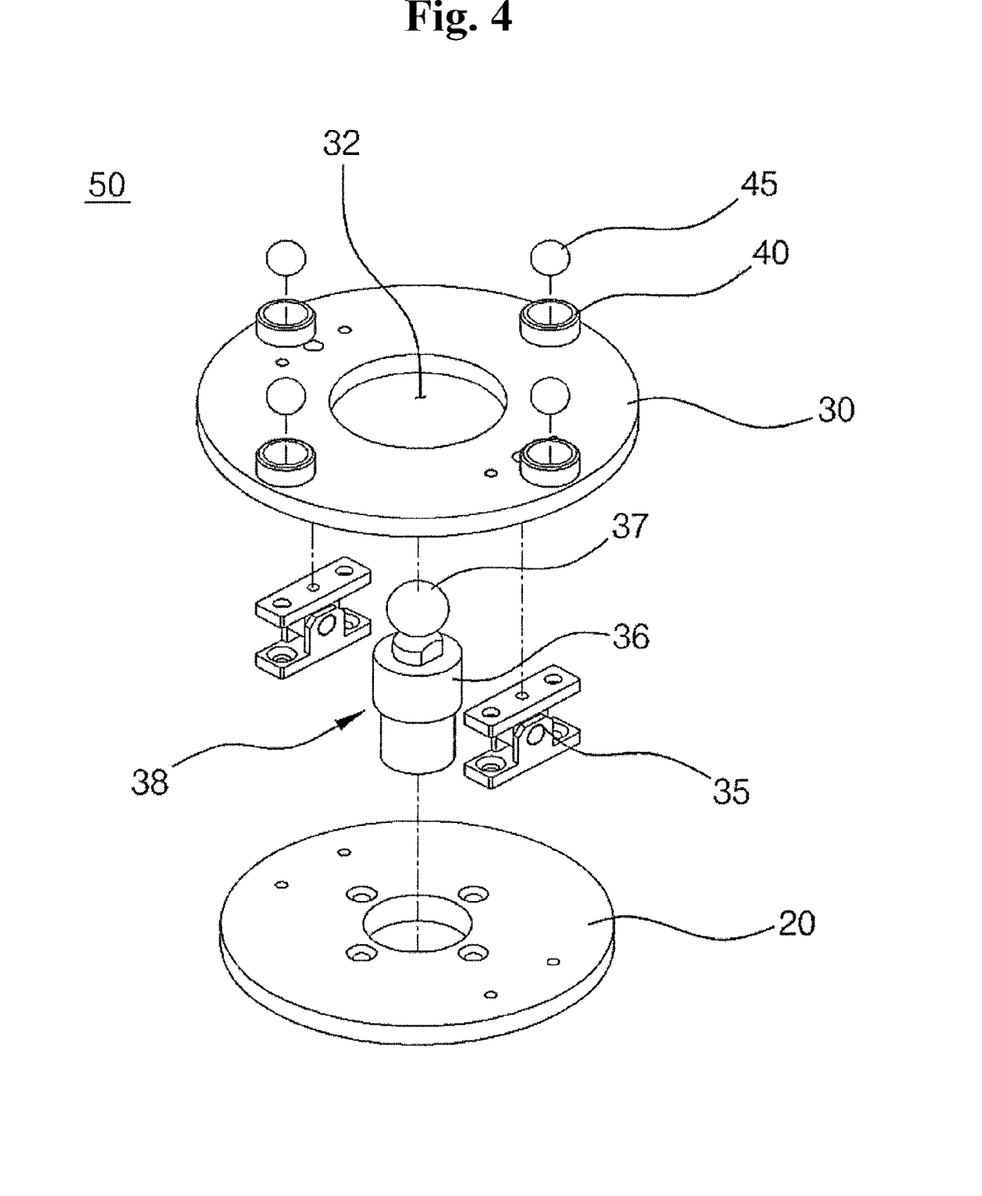
FIG. 4 is an exploded perspective view of the rotating part of the rotation driving device for cell culturing as shown in FIG. 1.

FIG. 3 is a perspective view of the rotating part (50) of the rotation driving device (100) for cell culturing and FIG. 4 is an exploded perspective view of the rotating part (50) of the rotation driving device (100) for cell culturing.

As described in FIGS. 3-4, the rotational part (50) includes a rotational shaft (38) of which one end is coupled to the motor (10) and which is rotated by the power supplied from the motor (10), a circular plate type first supporting part (20) disposed at a lower end of the rotational shaft (38) to rotatably support the rotational shaft (38), a circular plate type second supporting part (30) which is disposed at an upper side of the first supporting part (20) and connected with the first supporting part (20) through a hinge member (35) and which is formed with an opening (32) at a center portion thereof, a ball bearing receiving part (40) which is formed on circumference of the upper surface of the second supporting part (30) and formed with a spherical recessed portion in which a part of a ball bearing is received, and a ball bearing (45) to be rolled in the ball bearing receiving part (40).

The rotational shaft (38) fixed to the motor (10) is formed of a rod shape that its body (36) has a circular section. In addition, the rod can have a square section, a triangular section and the like where it is fixed to the motor (10).

In the angular end of the rotational shaft (38), which is contacted with a power transmitting part (70) of the driving part (80), it is apprehended that the end is worn away due to its rotation or a component is damaged. Therefore, it is preferable that the rotational shaft (38) has a spherical end (37).

The first supporting part (20) disposed at the lower end of the rotational shaft (38) fixed to the motor (10) allows the rotational shaft (38) to be rotatably supported, and the rotational shaft (38) passes through a center portion of the first supporting part (20). Preferably, a circular plate is used as the first supporting part (20) to maintain a stable-balanced state upon the rotation thereof, but other types are also used.

A first supporting part fixing portion (25) is provided at a lower side of the first supporting part (20) and permits to fix the first supporting part (20) with the rotational shaft (38). In other words, if the rotational shaft (38) is rotated while only the first supporting part (20) is coupled to the rotational shaft (38), there is the possibility that the first supporting part (20) is separated from the rotational shaft (38) by gravity or centrifugal force. Therefore, the first supporting part fixing portion (25) has a role of supporting the first supporting part (20).

In addition, the first supporting part fixing portion (25) functions to support a load of the first supporting part (20). Therefore, first supporting part fixing portion 25 is formed of an elastic member like rubber.

The second supporting part (30) is disposed at the upper side of the first supporting part (20), and the hinge member (35) is interposed between the first supporting part (20) and the second supporting part (30) to supporting the second supporting part (30).

The hinge member (35) is disposed so that a central axis thereof is positioned at a center portion of both contacting portions. Therefore, unlike a general hinge member of which a central axis exists at one side thereof and thus which can be pivoted only in one direction, the hinge member (35) of the present invention can be freely pivoted in a clockwise or counterclockwise direction.

The second supporting part (30) is operated to be corresponding to a cell culture device receiving part (60). A lower surface of the second supporting part (30) is connected with the first supporting part (20) through the hinge member (35), and the load of the second supporting part (30) is dispersed to the first supporting part (20) through the hinge member (35).

A center portion of the second supporting part (30) is formed with an opening (32), and the spherical end (37) of the rotational shaft (38) is protruded upward through the opening (32), so that it is engaged with the power transmitting part (70) of the driving part (80).

The cylindrical ball bearing receiving part (40) having the spherical recessed portion is formed on circumference of the upper surface of the second supporting part (30) to receive a part of the ball bearing (45).

The ball bearing (45) is inserted into the recessed portion of the ball bearing receiving part (40) to be rolled. Since a large quantity of frictional heat is generated due to friction between the ball bearing receiving part (40) and the ball bearing (45), it is preferable that the ball bearing receiving part (40) is formed of a heat-resisting material.

Preferably, the ball bearing receiving part (40) and the ball bearing (45) inserted into it are formed at least three places to prevent the driving part (80) interlocked with the ball bearing (45) from being out of balance. In case there are provided three ball bearing receiving parts (40), the ball bearing receiving parts (40) are disposed to be spaced apart from each other at an angle of 120°, resulting that the driving part (80) is operated in a balanced mode.

The second supporting part (30) of the rotation driving device (100) shown in FIGS. 3-4 is provided with four ball bearings (45) and four ball bearing receiving parts (40). The ball bearing receiving parts (40) are disposed to be spaced apart from each other at an angle of 90°, so that the driving part (80) is operated in a balanced mode.

Figure 5:
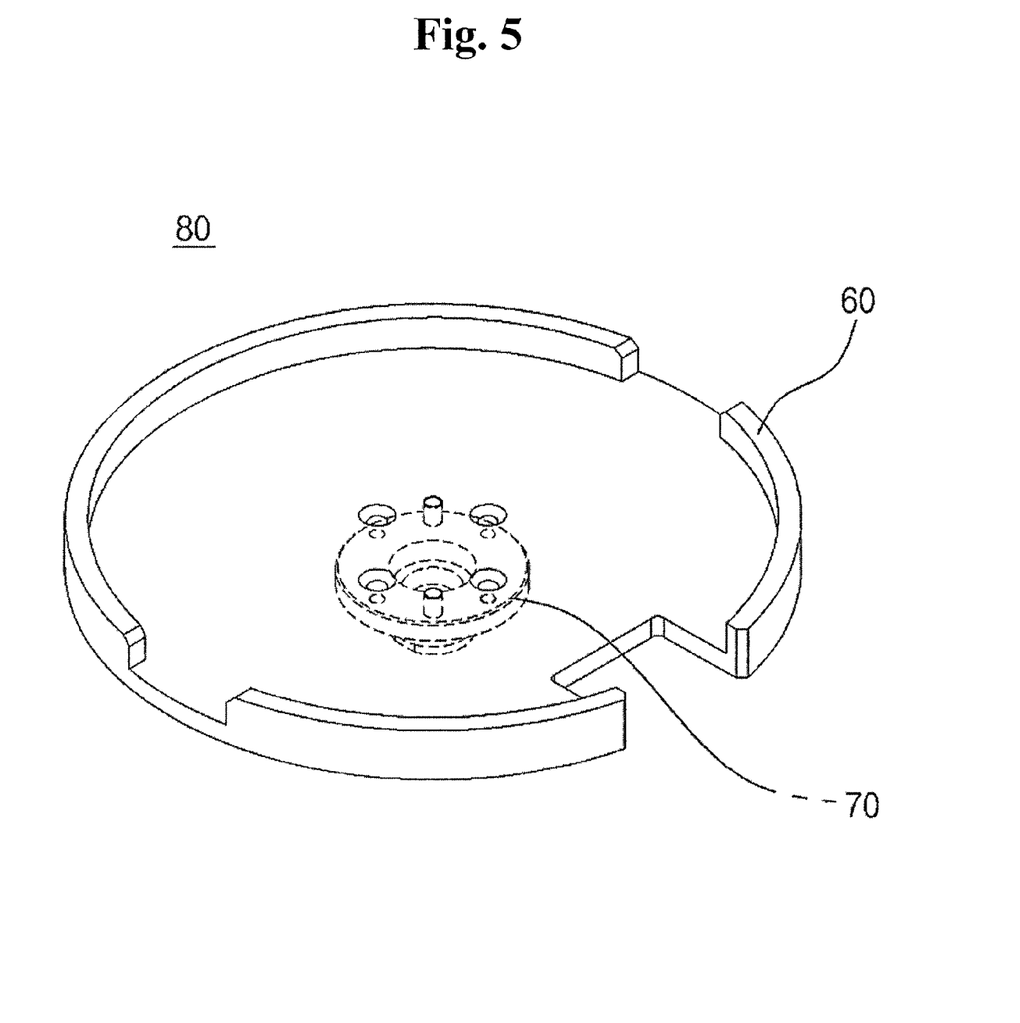
FIG. 5 is a perspective view of a driving part of the rotation driving device for cell culturing as shown in FIG. 1.
Figure 6:
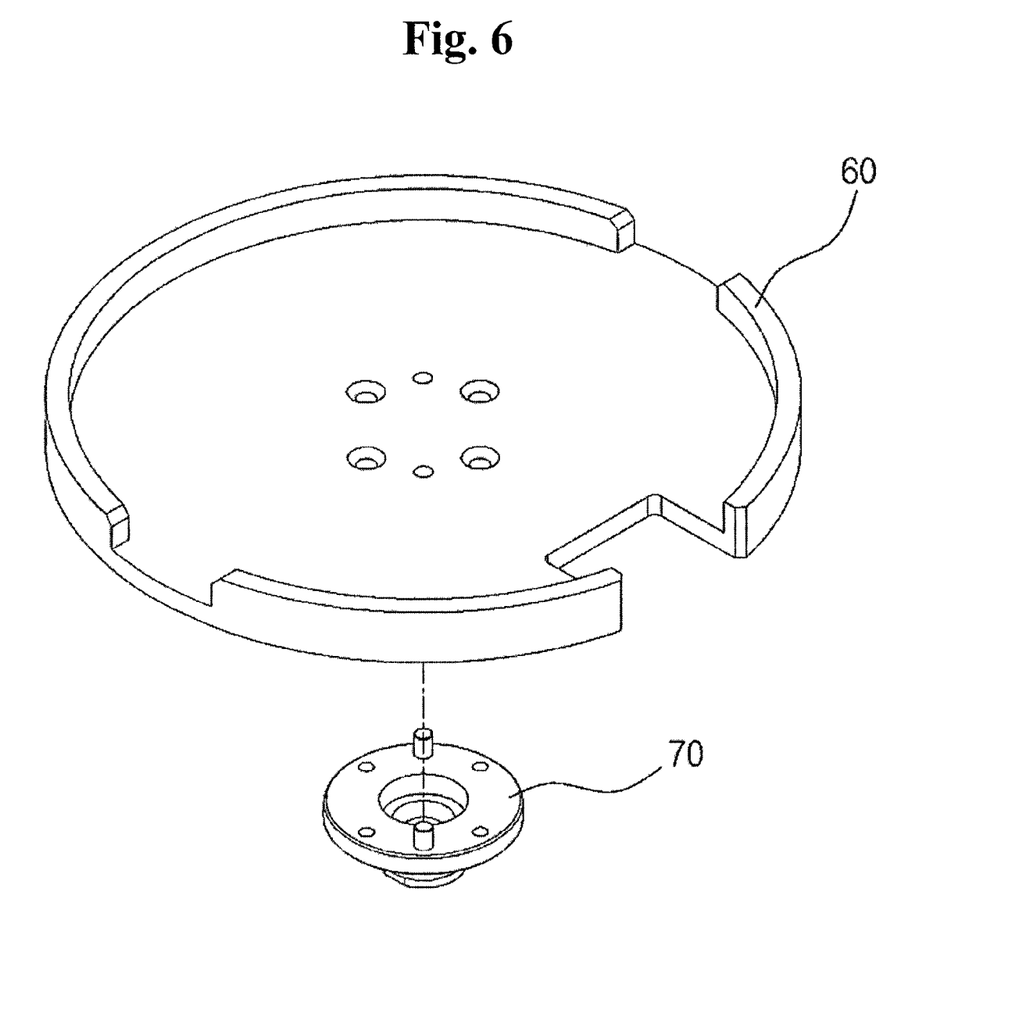
FIG. 6 is an exploded perspective view of the driving part of the rotation driving device for cell culturing as shown in FIG. 1.
Figure 7:
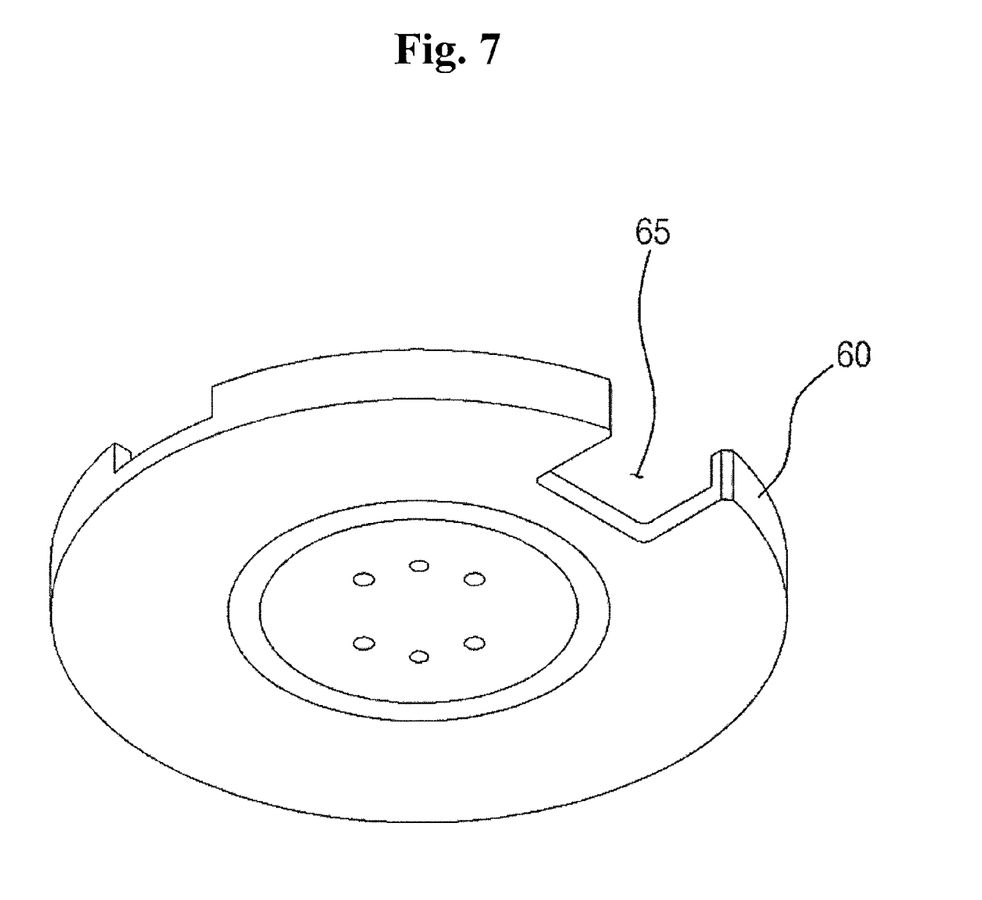
FIG. 7 is perspective view of a lower side of a cell culture device receiving part as shown in FIG. 1.
Figure 8:
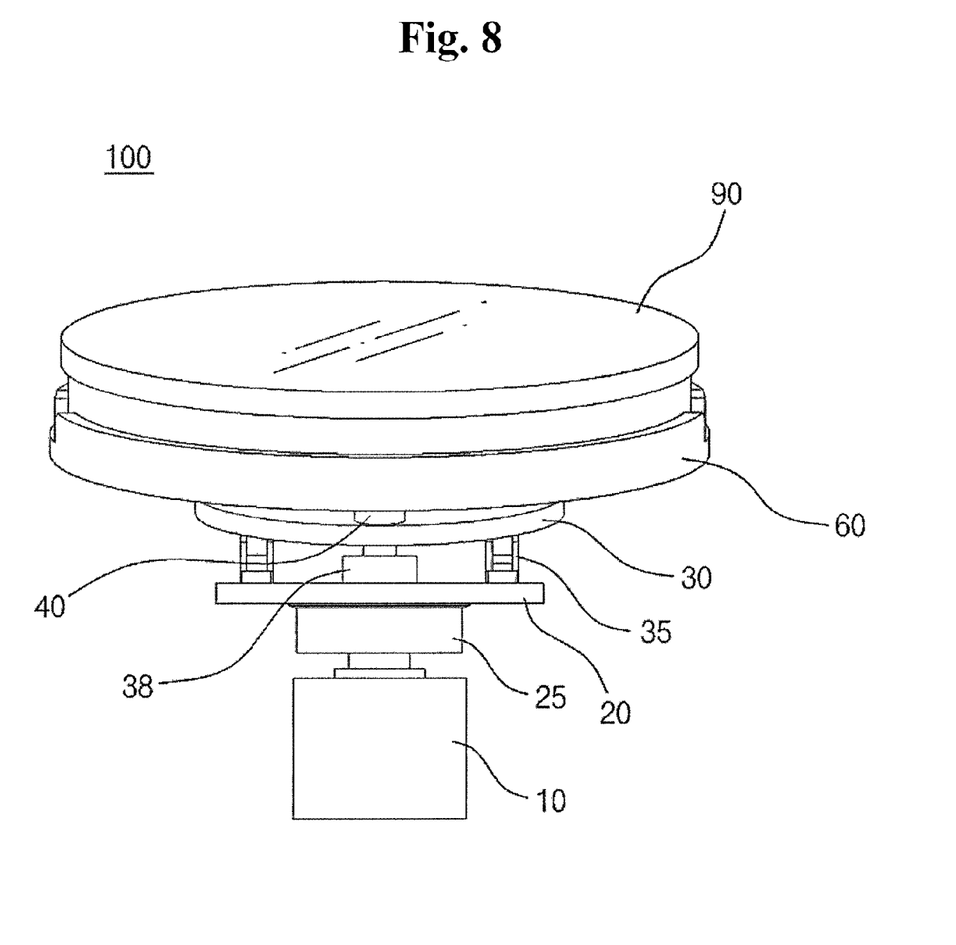
FIG. 8 is a view showing the rotation driving device that a cell culture device is mounted.

FIG. 5 is a perspective view of the driving part (80) of the rotation driving device (100), FIG. 6 is an exploded perspective view of the driving part (80) of the rotation driving device (100), and FIG. 7 is perspective view of a bottom side of the cell culture device receiving part (60).

Referring to FIGS. 5-6, the driving part (80) of the rotation driving device (100) includes a circular plate type cell culture device receiving part (60) which has an installation space to equip the cell culture device (90), and the power transmitting part (70) of which an upper surface is fixed to a bottom surface of the cell culture device receiving part (60) and a lower surface has a spherical recessed portion in which the spherical end (37) of the rotational shaft (38) of the rotational part (50) is pivotably inserted.

The ball bearing (45) of the rotational part (50) is directly contacted with the lower surface of the cell culture device receiving part (60). A ball bearing passage with an appropriate width is formed along a circumference of the lower surface of the cell culture device receiving part (60), so that the ball bearing (45) can be smoothly rolled.

As shown in FIG. 7, a plurality of grooves (65) is formed at a side surface of the cell culture device receiving part (60) to be detachable to the cell culture device in an easy manner.

Given to FIGS. 1-7, the operational principle of the rotation driving device (100) for cell culturing is described as follows:

In the motor (10) operated, the rotational shaft (38) fixed to the motor (10) is rotated. Thus, the first second supporting part (20) and the first supporting part fixing portion (25) fixed to the rotational shaft (38) are rotated according to the rotation of the rotational shaft (38), and the second supporting part (30) is also rotated because it is connected with the first supporting part (20) through the hinge member (35).

When the rotational part (50) is rotated as a whole, the ball bearing (45) disposed at the upper surface of the second supporting part (30) is rolled in a reverse direction to a rotational direction of the rotational part (50). This is caused by friction force generated between a contacted surface of the ball bearing receiving part (40) of the ball bearing (45) and a contacted surface of the cell culture device receiving part (60) of the ball bearing (45).

Since the ball bearing (45) is rolled in a reverse direction to a rotational direction of the rotational part (50), the cell culture device receiving part (60) contacted with the ball bearing (45) is not rotated but maintained in a stopped state. The spherical end (37) of the rotational shaft (38) is engaged with the power transmitting part (70) of the driving part (80), but since it does not exert an influence on the movement of the driving part (80) due to the rolling of the ball bearing (45), the driving part (80) is also maintained in the stopped state.

The second supporting part (30) and the cell culture device receiving part (60) interlocked with the second supporting part (30) are also inclined where the hinge member (35) is inclined to one side on its central axis for the rotation of the rotational shaft.

In the rotational part (50) rotated in a state inclined to one side, since the cell culture device receiving part (60) is maintained in the stopped state, it is periodically moved while only an inclination thereof is changed in the rotational direction of the rotational shaft (50).

In other words, as the cell culture device receiving part (60) is inclined in an inclined direction of the hinge member (35) of the rotational part (50) and the inclined direction is changed due to the rotation of the rotational part (50), an inclined direction of the cell culture device receiving part (60) is also changed. However, the cell culture device receiving part (60) is not rotated due to the rotation of the ball bearing (45).

Due to repeat of such motion as described above, the cells cultured in the cell culture device receiving part (60) are uniformly mixed, and the culture solution is equally distributed, whereby the cells in the cell culture device are evenly grown.

In addition, it is convenient since it is not necessary for the user to shake the cell culture device in a manual manner. And since a large friction force is not generated therein, it can be used for a long time period without any damage.

Furthermore, according to the present invention, it is possible to control a rotational speed of the rotational part by providing a separate automatic control unit.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A rotation driving device for cell culturing, comprising:
a power supplying unit which is operated by receiving electric power from an outside;
a rotational part which is rotated by the power supplying unit; and
a driving part which is provided at an upper side of the rotational part and maintained in a stopped state when the rotational part is rotated so that only an inclination of the driving part is changed according to a rotational direction of the rotational part, wherein the rotational part comprises (a) a rotational shaft which is fixed with the power supplying unit at its one end and is rotated by the electric power supplied by the power supplying unit; (b) a circular plate type first supporting part attached to a lower end of the rotational shaft to support it for its rotation; (c) a circular plate type second supporting part which is disposed at an upper side of the first supporting part and connected with the first supporting part through a plurality of hinge members and which is formed with an opening at a center portion thereof; (d) ball bearing receiving parts which are formed on a circumference of an upper surface of the second supporting part and with a spherical recessed portion to receive a part of a ball bearing; and (e) ball bearings which are received in the ball bearing receiving part to be rolled.

2. The rotation driving device according to claim 1, wherein the power supplying unit comprises a motor operated by the external electric power.

3. The rotation driving device according to claim 1, wherein the rotation driving device further comprises a first supporting part fixing portion which is provided at a lower side of the first supporting part to fix the first supporting part.

4. The rotation driving device according to claim 1, wherein the rotational shaft is formed into a rod shape with a circular section, and the other end of the rotational shaft, which is not fixed to the power supplying unit, has a spherical shape.

5. The rotation driving device according to claim 1, wherein the ball bearing receiving part is formed at least three places on the circumference of the upper surface of the second supporting part to be spaced apart from each other in regular intervals.

6. The rotation driving device according to claim 1, wherein the hinge member is provided between the first and second supporting parts so that a central axis thereof is positioned at a center portion of both contacting portions and thus an angle thereof is controlled in both directions.

7. The rotation driving device according to claim 1, wherein the driving part comprises:
 a circular plate type cell culture device receiving part which has an installation space to equip the cell culture device; and
 a power transmitting part of which an upper surface is fixed to a bottom surface of the cell culture device receiving part and a lower surface has a spherical recessed portion in which the spherical end of the rotational shaft of the upper rotational part is pivotably inserted.

8. The rotation driving device according to claim 7, wherein the lower surface of the cell culture device receiving part is contacted with a ball bearing passage formed along a circumference thereof to have an appropriate width so that the ball bearing of the rotational part can be rolled.

9. The rotation driving device according to claim 7, wherein a plurality of grooves are formed at a side surface of the cell culture device receiving part so that the cell culture device can be easily installed and separated.

* * * * *